(12) United States Patent
Brooks et al.

(10) Patent No.: US 11,764,949 B2
(45) Date of Patent: Sep. 19, 2023

(54) SECURE ELECTRONIC HEALTH RECORD ACCESS DURING AN EMERGENCY MEDICAL EVENT

(71) Applicants: David Andrew Brooks, San Jose, CA (US); Davis Zhu, Fremont, CA (US)

(72) Inventors: David Andrew Brooks, San Jose, CA (US); Davis Zhu, Fremont, CA (US)

(73) Assignee: SEMCOREL INC, San Jose, CA (US)

(*) Notice: Subject to any disclaimer, the term of this patent is extended or adjusted under 35 U.S.C. 154(b) by 163 days.

(21) Appl. No.: 16/416,204

(22) Filed: May 18, 2019

(65) Prior Publication Data
US 2020/0366473 A1    Nov. 19, 2020

(51) Int. Cl.
| | |
|---|---|
| *H04L 29/06* | (2006.01) |
| *H04L 9/08* | (2006.01) |
| *H04L 9/32* | (2006.01) |
| *G06F 21/62* | (2013.01) |
| *G16H 10/60* | (2018.01) |
| *G16H 15/00* | (2018.01) |
| *H04L 9/30* | (2006.01) |

(52) U.S. Cl.
CPC ........ *H04L 9/0833* (2013.01); *G06F 21/6245* (2013.01); *G16H 10/60* (2018.01); *G16H 15/00* (2018.01); *H04L 9/0866* (2013.01); *H04L 9/0891* (2013.01); *H04L 9/0894* (2013.01); *H04L 9/30* (2013.01); *H04L 9/3236* (2013.01); *H04L 2209/38* (2013.01)

(58) Field of Classification Search
CPC ... H04L 9/0833; H04L 9/0866; H04L 9/0891; H04L 9/0894; H04L 9/3236; H04L 9/30; H04L 2209/38; H04L 9/3239; H04L 2209/88; G06F 21/6245; G16H 10/60; G16H 15/00
See application file for complete search history.

(56) References Cited

U.S. PATENT DOCUMENTS

| | | | |
|---|---|---|---|
| 10,594,484 B2* | 3/2020 | Rodriguez | ............ H04L 9/0822 |
| 2006/0229911 A1* | 10/2006 | Gropper | ................ G16H 30/20 |
| | | | 705/2 |
| 2007/0027715 A1* | 2/2007 | Gropper | ................ G16H 10/60 |
| | | | 705/2 |
| 2007/0192140 A1* | 8/2007 | Gropper | ................ G16H 10/60 |
| | | | 705/3 |
| 2014/0047513 A1* | 2/2014 | van 't Noordende | ...................... |
| | | | H04L 63/0823 |
| | | | 726/4 |

(Continued)

*Primary Examiner* — Mahfuzur Rahman
(74) *Attorney, Agent, or Firm* — Helen Mao; Imperium Patent Works (57) ABSTRACT

Access to Electronic Health Records (EHR) is protected by law in many countries, including the US through HIPAA. During an emergency medical situation however, access to this information by the Emergency Care Team (ECT) may save the life of the Person In Distress (PID). The present invention describes a system and method for managing the access to EHRs based on the membership in a pre-established ECT and the communication status of the ECT Members during an Emergency Event. This invention includes a method of Encryption key exchange to ensure EHRs are only shared with authorized participants during the emergency event. This system and method further provides for the secure and immutable recording of the individuals who accessed the EHRs during this emergency event.

10 Claims, 12 Drawing Sheets

(56) References Cited

U.S. PATENT DOCUMENTS

2015/0278449 A1\* 10/2015 LaBorde ................ G16H 10/60
705/3

\* cited by examiner

SECURE ELECTRONIC HEALTH RECORD ACCESS DURING AN EMERGENCY MEDICAL EVENT

BACKGROUND ART

The Privacy Rule, a Federal law, gives you rights over your health information and sets rules and limits on who can look at and receive your health information. The Privacy Rule applies to all forms of individuals' protected health information, whether electronic, written, or oral. The Security Rule is a Federal law that requires security for health information in electronic form.

EHRs are most commonly stored in the cloud today, to facilitate sharing with authorized individuals. This architecture also makes a tempting target for hackers which is why these records are usually encrypted at rest. This makes the key management very important. The present invention provides a secure method of unlocking health information only during a medical emergency and only by the members of the ECT based on their membership in that team.

Privacy Preserving EHR System Using Attribute-based Infrastructure By Shivaramakrishnan Narayan, Martin Gagné and Reihaneh Safavi-Naini discusses the use of public key encryption to include Access based on an Attribute Set associated with 3rd parties where this Attribute set determines who can view these records. The present invention does not rely on attributes embedded with the Records, but on a group of individuals who have been invited and accepted membership in an ECT. Membership in the ECT provides access only during an Emergency Event.

U.S. Pat. No. 9,667,599 granted to Hu and Weaver "A dynamic, context-aware security infrastructure for distributed healthcare applications" describes a system where a Plurality of verified third parties are used to determine if the user has a right to view the EHRs. Our system relies on membership in a predefined team which is authorized by the Person whose records are to be shared on during an emergency event.

Application US20170262639 filed 2017 Sep. 14 by Roy Peter D'Souza et al "Cloud key escrow system" relies on a plurality of verified third parties to provide authorization for access, where a threshold number of replies must be received. Our invention does not rely on third party authorizations.

U.S. Pat. No. 8,041,749 Granter Oct. 18, 2011 to Michael E. Beck "Systems and methods of managing specification, enforcement, or auditing of electronic health information access or use" This patent claims a system where a first user modifies the access rights of a second user, but doing so based on the first user's relationship to the health information using a table of relationships to determine if the first user has at least an indirect relationship to the subject. Our invention does not rely on a relationship during the emergency. We are not directing a user to modify the data access, our software is automatically granting access to the members of a list. Further we are not receiving an access request for modification from a user.

U.S. Pat. No. 8,352,287 granted to Robert H. Lorsch Granted Jan. 8, 2013 "Method for proving a user with a service for accessing and collecting personal health records" relies specifically on fax based health records received from health care providers.

US20130179195 application by Lorsch "Method and system for managing personal health records with telemedicine and health monitoring device features" describes a system whereby a person refers to creating EHR from Monitoring data and making that data available to health care providers at the user's request.

U.S. Pat. No. 8,645,161 granted to Lorsch Feb. 4, 2014 "Method and system for providing online records" describes a system where the user receives and actively files their medical records in a plurality of folders.

U.S. Pat. No. 8,984,583 granted Mar. 17, 2015 to Bhatti and Martin "Healthcare privacy breach prevention through integrated audit and access control" describes a specific method of implementing compliance for privacy involving the reduction of logs and the creation of Role-Access pairs. Our invention uses a different method.

Application US20160292453 by Patterson and Malec Mar. 31, 2015 "Health care information system and method for securely storing and controlling access to health care data" involves the use of Circuitry.

Application US20150332283A1 by Witchey "Healthcare transaction validation via blockchain proof-of-work, systems and methods" uses blockchain to encode healthcare transactions with a validity component whereas our invention uses blockchain to encode access events.

U.S. Pat. No. 9,135,608B2 granted Sep. 15, 2015 to Sten Herlitz "Systems and methods for constructing a local electronic medical record data store using a remote personal health record server" describes a remote DB accessible to a clinician and a local DB accessible only to the Patient. Our Cloud DB is not accessible to clinicians and in our invention we do not persist the EH Records in the User Endpoint Devices, but present during an emergency as needed.

U.S. Pat. No. 8,904,501 granted Dec. 2, 2014 to Wallace J. Luke et al "Method and system for automated emergency access to medical records" describes a method for emergency responders that relies on a web site with "a button activated interface wherein the button activated interface triggers an automatic access number generator for displaying a web page with an emergency access card" which is not part of our invention.

A Dynamic, Context-Aware Security Infrastructure for Distributed Healthcare Applications by Junzhe Hu and Alfred C. Weaver, Department of Computer Science University of Virginia Charlottesville, VA 22904 "Third, the security requirements in our healthcare system require very dynamic and flexible policy enforcement. Even in the normal case, there are many intricate user-data relationships that must be managed by the security framework; in addition, we must also accommodate emergency access to data in life-threatening situations (e.g., public health emergency). In our proposed security infrastructure, the policy enforcement mechanism is highly dynamic and independent from any particular application."

U.S. Pat. No. 8,352,287 granted to Robert H. Lorsch Method for proving a user with a service for accessing and collecting personal health records (MymedicalRecords Inc) This patent provides individuals with immediate access to healthcare records in emergency situations to assist in providing appropriate care but relies on EHRs received by fax from at least one health provider. Our system does not rely on faxed information.

SUMMARY OF THE INVENTION

Our invention involves the temporary unlocking of Electronic Health Records(EHRs) on behalf of a person who is experiencing a medical emergency and the secure delivery of relevant portions of those records to their Emergency Care Team (ECT). It is important to note that while a person may be willing to share private medical information with another individual during a medical event, they may not be willing to share the same information outside of the emergency. This means the access is not persistent based on the relationship. The temporary access based on a verified medical emergency and the membership in an ECT is a key aspect of this invention.

Prior to the emergency event, a person (caree) invites one or more friends, neighbors, family members, or professional care providers to participate in their ECT based on the trust they have in these people and the physical proximity of the individuals to the caree's home. The invitees have a choice of accepting or rejecting this invitation and the responsibilities it entails.

If the invitation is accepted, each member is provided with a shared private Encryption key to be used by each group member during the process described below. Membership in the ECT is also logged by storing the members' Globally Unique ID (GUID) and emergency contact information in the system's database.

The public encryption key associated with the ECT is stored in the system database associated with the caree for use during an emergency event.

During an emergency involving the caree, ECT members will be notified. As part of the notification, the private key, which is pre-encrypted by the ECT's public key, of the Person in Distress (PID) is securely transmitted to the ECT members. The encrypted EHRs of the PID are also transmitted to the ECT members who will now be able to view the health information as part of the Emergency response.

ECT members will access the EHRs using a user endpoint device and software. In the most common embodiment they will use an App on their mobile phone. In other embodiments, they will access the system through a browser on a mobile phone, laptop, tablet, or embedded screen such as the screen in an automobile. In both cases, the user must authenticate to access the Emergency Response Page (ERP).

Other participants may be temporarily added to the ECT at the discretion of the existing team members. For example, emergency medical technicians (EMTs) or other medical service providers may be given access to a web based page to assist in treatment. Their contact information is added to the system to track their access to the health records. They are granted a temporary Globally Unique ID (GUID) and temporary membership in the ECT.

When a new temporary member is added to the ECT, they will not have the same setup as the existing long term ECT members. In particular, they will not possess the ECT private key, nor any preloaded app in their endpoint device. This invention includes a cloud based virtual session which is accessed by newly added temporary ECT members. Users of this temporary session will request access to the EHR from the ECT member who invited them to join. That member's endpoint device will render the EHR information into hits format, for example an image or PDF, suitable for display by the Temporary ECT member's Viewing device. This bits will be sent to the Temporary member's virtual session by the Inviting member's endpoint device which will then display the bits to the new member. The bits is not cacheable at the new member's endpoint device. This virtual session will be destroyed at the conclusion of the emergency event, eliminating future access by the Temporary ECT member.

Another aspect of this invention is the use of an immutable technology to provide an audit history of access events. The Audit history logs all access of EHRs. For each access the system records:

The PID Identity,
Which Health Records shared,
Date & Time of access, and
GUID of the person who accessed.

As the event progresses, any access of EHRs is logged with the information above. Temporary members of the ECT will be issued a GUID when added with their name and contact information stored in the Database. Their access events will be logged just like the long term ECT members. When the Emergency event completes, these access logs are incorporated into a secure and immutable record which is distributed to the long term ECT members' endpoint device as well as the caree's endpoint device. (Temporary ECT members do not get a copy of this log.) A further copy is saved in the Database associated with the caree. The technology used and distribution of this record to a plurality of storage locations makes it difficult to alter any one of the records without detection. One implementation of this is to use Blockchain to encode the records.

BRIEF DESCRIPTION OF THE DRAWINGS

FIGS. 6.1 and 6.2 shows how the caree's private key can be securely recovered if it is lost.

DETAILED DESCRIPTION

Figure 1:
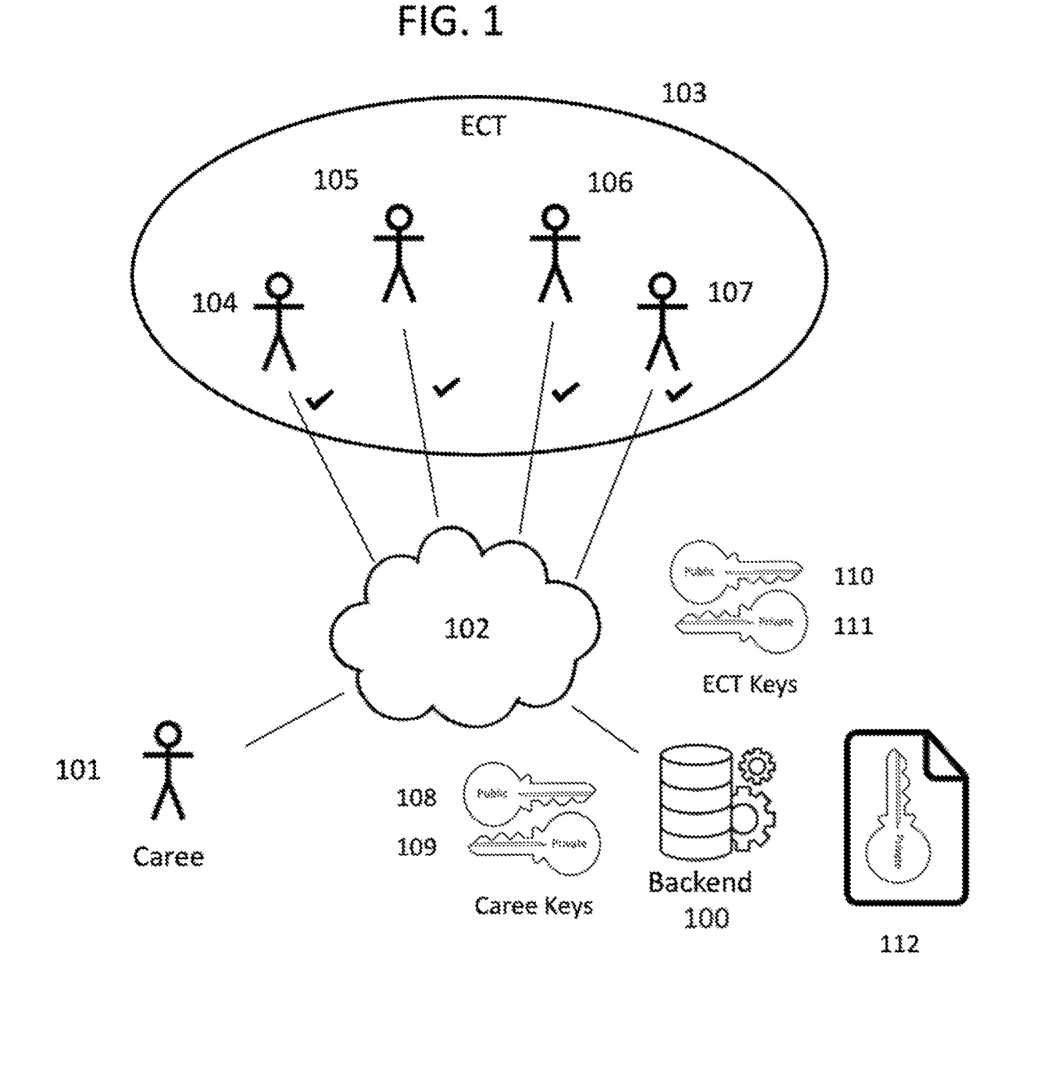
FIG. 1 shows the first step of the initial setup of the Emergency Care Team.
Figure 2:
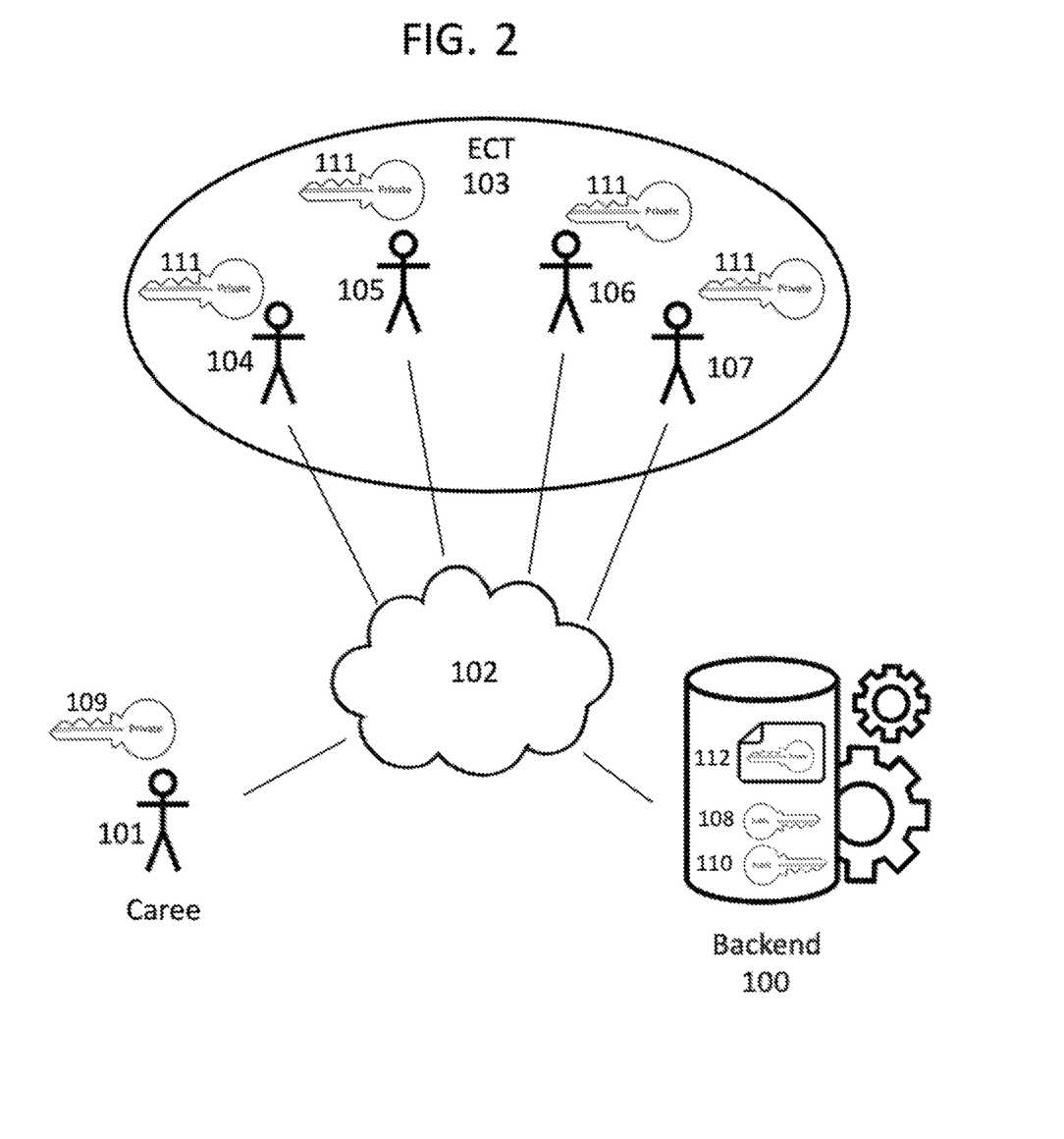
FIG. 2 shows the distribution of private keys to caree and ECT
Figure 3:
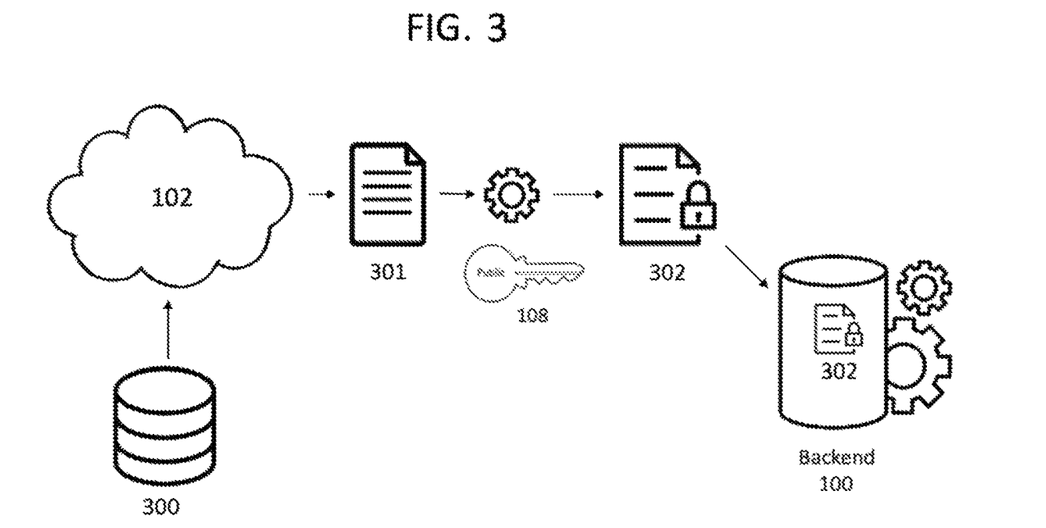
FIG. 3 shows how the Unencrypted Electronic Health Records of the caree are encrypted for Secure storage on the Backend Server

FIGS. 1 through 3 show the initial setup of the Emergency Care Team (ECT) and data structures.

FIG. 1 shows a backend system (100) which provides shared computing resources for all carees, an invited subset of their friends, family, and caregivers and consisting of at least one instance of a cloud hosted processing element, working memory, and nonvolatile memory with communications over a broadband network using IP based protocols. The caree (101) instructs the backend system (100) to create the ECT (103) by transmitting a message through the Communications Cloud (102). In this example four members (104-107) are invited to join the ECT also by transmitting a message through the Cloud (102) and all have accepted the invitation. Actual team size will vary by individual users of the system. The system (100) generates two pairs of public and private keys. The first pair of keys (108 and 109) is for the caree (101). The Second pair of keys (110 and 111) is for the ECT (103). The system then takes a copy of the caree private key (109) and encrypts it using the public key of the ECT (110) creating an encrypted document (112).

In FIG. 2, the Backend Server (100) distributes the caree's private key (109) to the caree's endpoint device for storage and deletes it from System Memory. The Backend no longer has an unencrypted copy of the caree private key. The caree's public key (108) is stored in nonvolatile system memory for later use. The Backend then distributes the ECT private key (111) to the endpoint device of all members of the ECT (103) who have accepted the invitation and Deletes the ECT private key from System Memory. The Backend no longer has a copy of the ECT private key (111). The Backend Stores the ECT public key (110) in nonvolatile system member for later use. Finally the System stores the Encrypted document of the caree private key (112) in nonvolatile system member for future use In FIG. 3, The Backend Server (100) requests Electronic Data Records (301) from one or more EHR Repositories (300) based on the caree's rights of access. As the EHRs arrive through the Communication Cloud (102), the Backend Server (100) retrieves the caree's public key (108) and uses it to encrypt each and every EHR to create an encrypted EHR (302). This Record is then stored in the nonvolatile memory for future use. The system then deletes the Clear EHRs (301) from all memory. Note that the Backend Server does not have an unencrypted private key for the caree, so it is not possible for the system to decrypt the retained records (302) and neither is it possible for hackers to decrypt these EHRs even if they breach the security of the Backend server (100).

Figure 4:
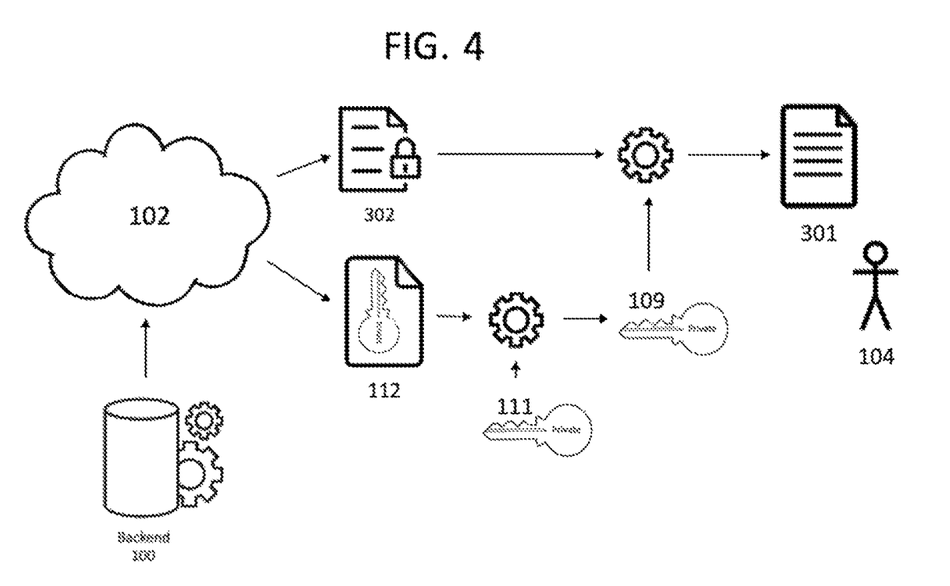
FIG. 4 shows how during an emergency, the encrypted EHRs of the caree are securely transmitted to all members of the ECT such that they can decrypt them on their Endpoint Devices.

FIG. 4 shows the process that occurs during an emergency event. The Backend Server (100) sends two documents from its nonvolatile memory across the Communication Cloud (102) to every member of the ECT as they join the emergency call; the encrypted EHRs (302) and the encrypted document containing the caree's private key (112). This figure shows a representative ECT member (104). The end point computing device of the ECT member will first decrypt the caree's private key (109) using their ECT private key which was stored in the ECT members' Endpoint device's Nonvolatile memory. The End Point device then uses the caree's private key (109) to decrypt the encrypted EHRs (302) which produces a copy of the records in the clear, now readable to the ECT member (104) on their endpoint device.

Still referring to FIG. 4, when the Emergency call is complete, the ECT Member's endpoint device will delete the caree's private key (109) from memory and delete the caree's medical Records (301 and 302) from memory.

Figure 5:
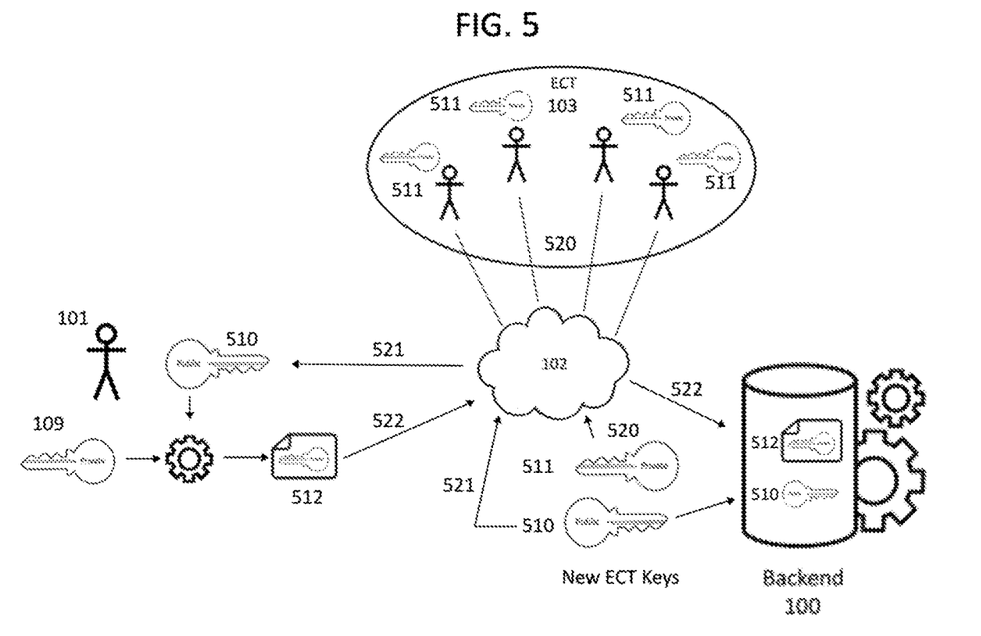
FIG. 5 shows how a new set of keys can be generated for the ECT members in the event one of them loses their Endpoint Device, a new ECT member is added, or an ECT member leaves the team.

FIG. 5 shows the secure method of updating the ECT public and private keys when any of the ECT members leave the group, a new member is added, or an ECT member loses private key. The Backend server (100) generates a new pair of ECT keys (510 and 511). The new private key (511) is securely sent in a message (520) directly to all of the ECT members across the Communication Cloud (102). The ECT members store their key in nonvolatile memory on the endpoint device for future use. The New ECT public key (510) is first stored in the Backend Nonvolatile memory to replace the previous version. The New ECT public key (510) is then sent to the caree (101). The caree's endpoint device encrypts the caree private key (109) using the ECT public key (510) and created an encrypted document (512). This document is sent in a message (522) to the Back End (100) over the Communications Cloud (102) where the Back End stores the document (512) in nonvolatile memory for future use. All of the keys which rely on the ECT public or private keys are now updated.

Figure 61:
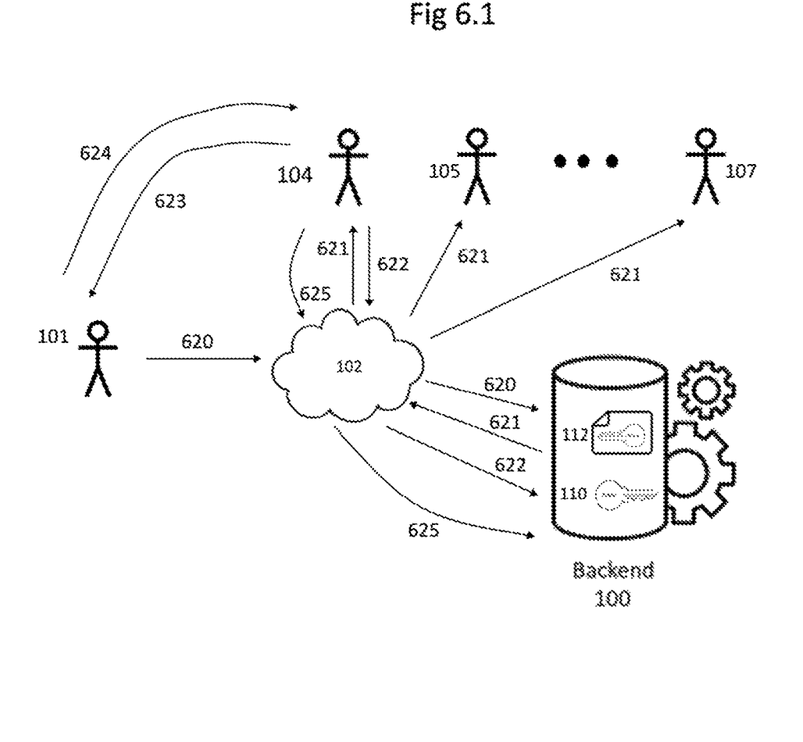

FIG. 6.1 shows the first step of a secure method for updating the caree public and private key when the caree Loses their endpoint device. The Medical Records in the Backend Server are already encrypted with the caree public key. Instead of regenerating a new key pair, it is more expedient to recover the key and send to the caree. The backend server (100) receives a message (620) from the caree (101) indicating their private key is lost. The backend server (100) will broadcast of request (621) to all ECT members to ask for confirmation that the caree needs recovering their key. This is necessary to prevent a bad actor from spoofing the caree. At least one ECT member (104) confirms they will assist through a message (622). The ECT member then contacts the caree using a different channel such as a phone call or an email (623) to confirm they made the request (620). If the caree confirms (624), the ECT member will confirm the request by sending a message (625) to the Backend Server (100).

Figure 62:
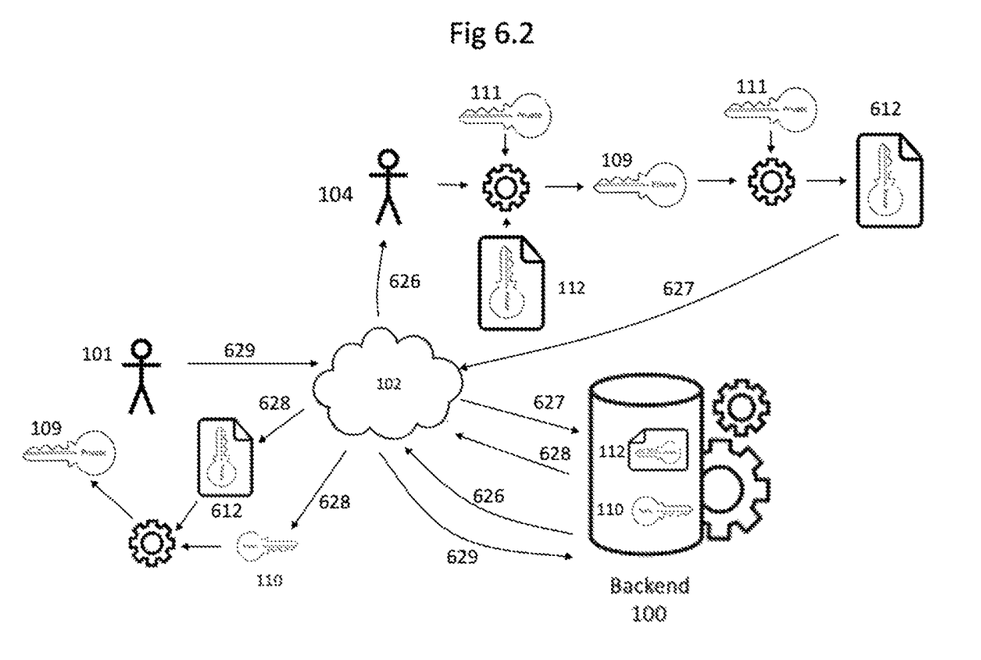

FIG. 6.2 shows the second step of the caree key recovery process. With the confirmation from the response of its first member of ECT (104), the System will retrieve the Encrypted caree key (112) from nonvolatile memory and send it to the ECT Member's (104) Endpoint device in a message (626). The ECT Member's endpoint device will decrypt this message using their ECT private key (111) to retrieve the caree private key (109). The ECT Member Endpoint device will immediately encrypt this private key with their own ECT member private key (111) to create the secure document (612). The ECT member endpoint device will immediately delete the caree private key (109) from memory, and send this document (612) to the Backend Server (100) in a message (627) over the Communication Cloud (102). The Server will send both the Encrypted caree private key (612) and the ECT Member public key (110) to the caree's Endpoint Device in a message (628) over the Communication Cloud (102). The caree's endpoint device will then Decrypt the document (612) using the public key (110) to retrieve their private key (109) and store it in nonvolatile memory for future use. The caree's endpoint device will confirm recovery by sending a message (629) to the backend server (100) over the communication cloud (102).

Figure 7:
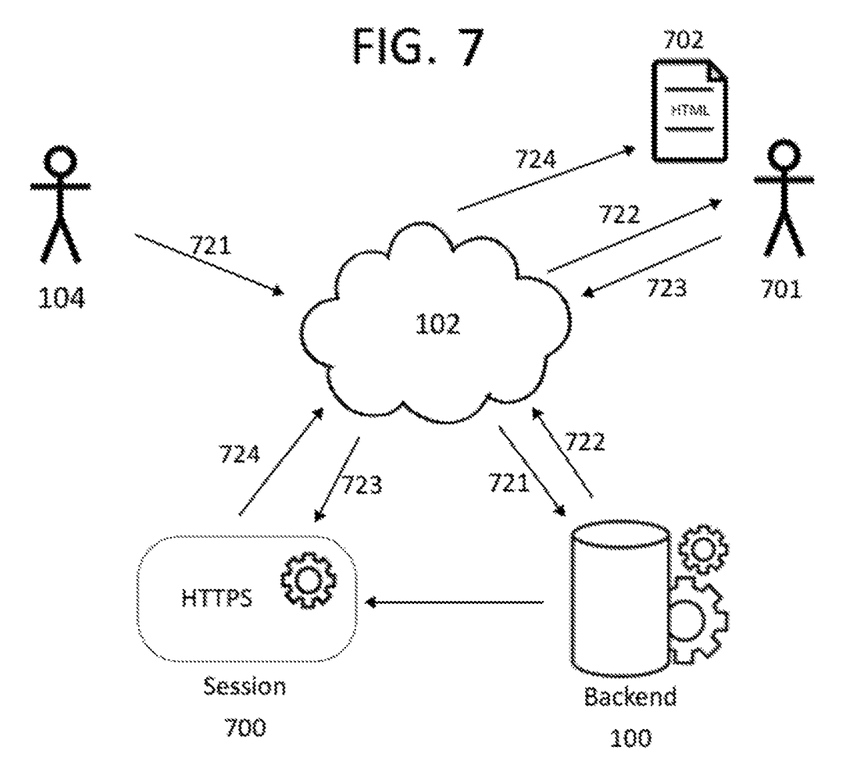
FIG. 7 shows how the Temporary ECT (TECT) member is added to the Emergency Event Session.

FIG. 7 shows how a Temporary ECT (TECT) Member is added to the Emergency Call. A message (721) is sent from ECT Member (104) to the Backend System (100) requesting a Temporary ECT member be added and providing contact information for the Temporary Member (701). The System creates a virtual session (700) to serve the new member and generates a message (722) containing a URL Link to the session and sends it to the Temporary ECT Member (701). The TECT member (701) Endpoint device requests a connection (723) to the Virtual Session (700). The Virtual session servers up a response (724) containing an HTML document (702) which represents the emergency call page.

Figure 8:
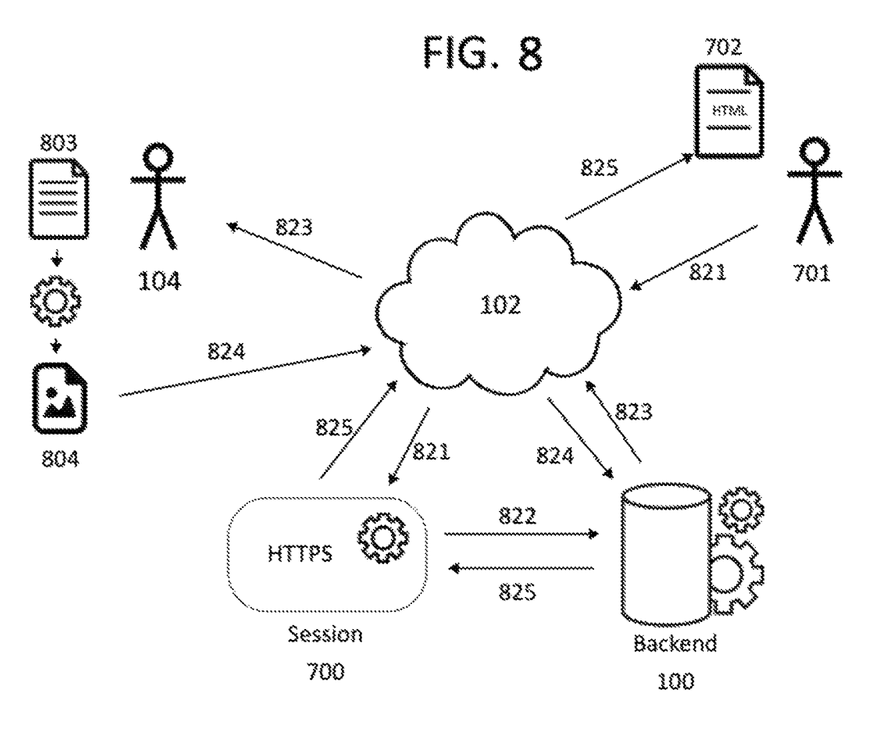
FIG. 8 shows how the TECT member requests access to the EHR and gains access without having an ET private key.

FIG. 8 shows how a Temporary ECT Member is able to view EHRs without an ECT private key. A request (821) is made from the HTML document (702) of the TECT member for the EHRs of the PID. The Virtual Session (700) Generates an API call (822) to the Backend which Generates a message (823) to the ECT Member's Endpoint device requesting the EHR. ECT Member (104) endpoint device renders the EHR data (803) into bits format (804), for example an Image or PDF, and returns the bits format in response message (824) to the Back End Server. The Backend Server Responds to the EHR request (822) by providing the bits in message (825) which is then sent back to the TECT member as the Response to their request (821) but marked as not cacheable. The bits is viewable by the TECT member (701) during the Emergency call, but once the call terminates, the bits is deleted from memory in the TECT member's endpoint device and the Secure Session (700) is deleted from working memory as well.

Figure 9:
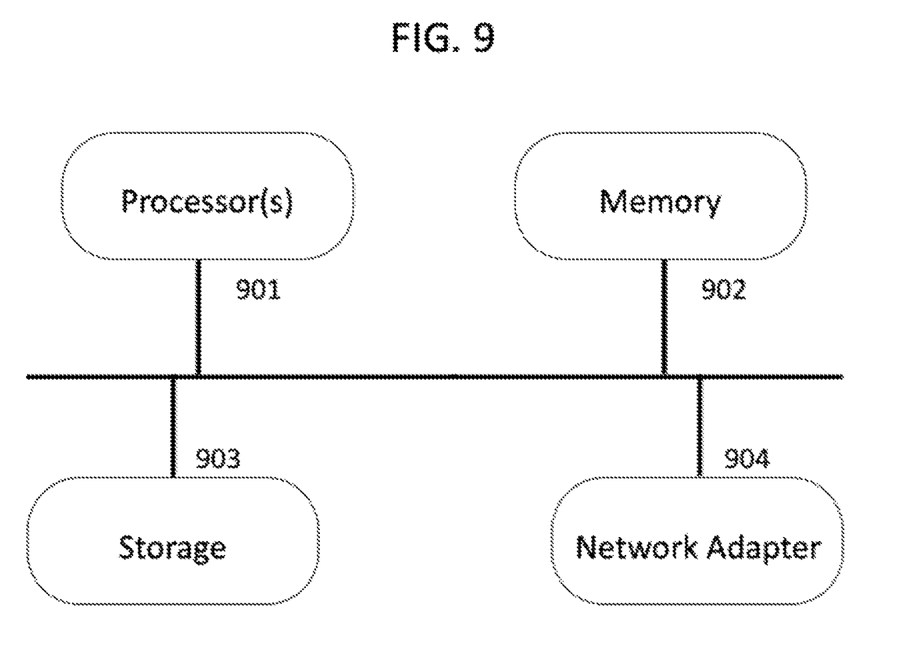
FIG. 9 shows our system architecture.

FIG. 9 shows the architecture of our backend system. At least one processing element (901) is connected to working memory (902) and storage or nonvolatile memory (903). The processing element is also connected to a Network Adaptor (904) which provides access to an internet for wide area communications.

Figure 10:
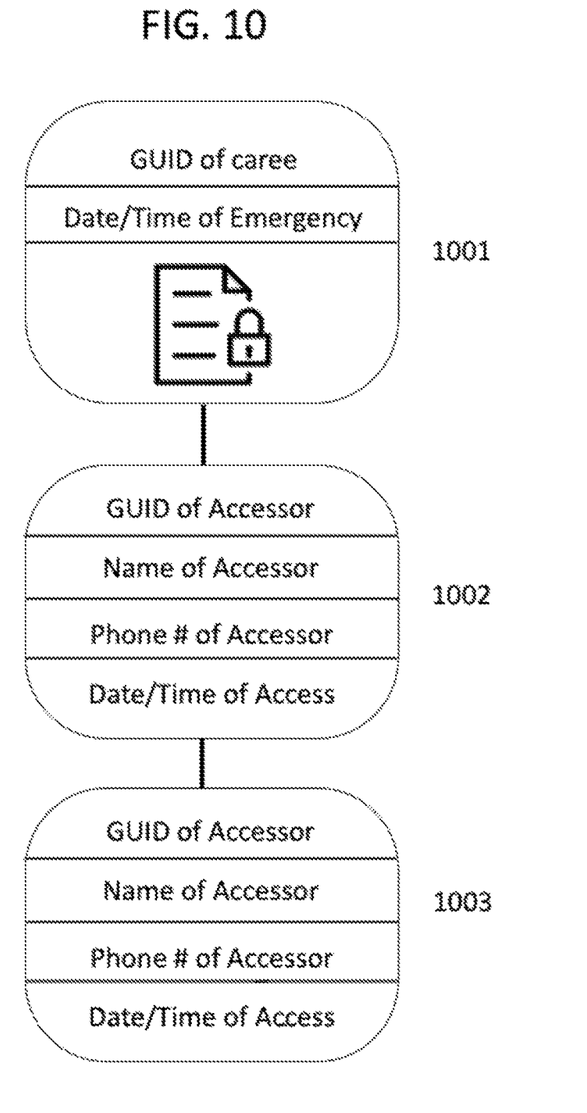
FIG. 10 shows how the system records access events to the EHRs during an emergency event.

FIG. 10 shows the structure of the access log which records the access of the EHRs during an emergency event. The backend system creates the initial record (1001) when the emergency event is confirmed. This record consists of the Global Unique ID (GUID) of the Person in Distress (PID), the date and time of the emergency event using Universal Coordinated Time (UCT), and a copy of the PID's EHRs (302) encrypted using the PID private key to establish what was being shared. For each ECT member who joins the emergency call and who views the EHRs, an access record is established and linked into the chain. Each access record consists of the GUID of the person who viewed the EHRs, the human readable name of the person who access the EHRs, the phone number of the person who accessed the EHRs, and the date and time of the access in UCT. Access record 1002 in FIG. 10 represents the first ECT member who viewed the EHRs and access record 1003 represents the subsequent person to access these records. The next person to view the EHRs will cause a new access record to be created and linked into the chain.

Figure 11:
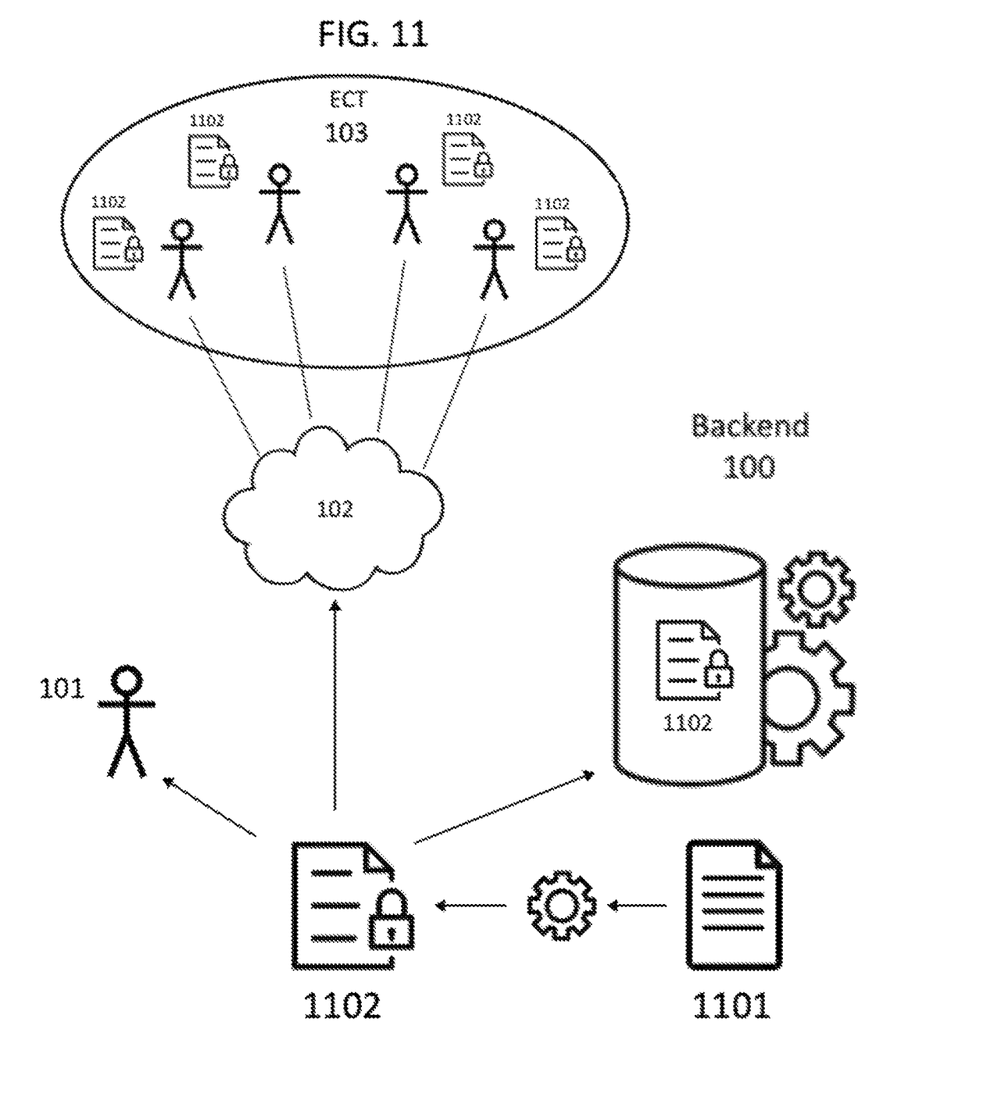
FIG. 11 shows how the system persists access events in a distributed and immutable method.

FIG. 11 shows the process that happens when the emergency call has completed. The access records (1101) as described above are transformed by the backend system (100) into an encrypted, immutable record (1002) and then transmitted across the communication network (102) to the endpoint device of each ECT member and to the endpoint device of the caree where the record is saved in nonvolatile memory of that person's endpoint device. A copy is also saved in the non-volatile memory of the backend server (100). In one embodiment of this invention, blockchain technology is used in this transformation.

The invention claimed is:

1. A method for providing access to Electronic Health Records (EHRs) based on the membership in a pre-established Emergency Care Team (ECT) associated with a caree and the communication status of the ECT members during an emergency call comprising:
   generating a public key & private key associated with ECT;
   generating a public key & private key associated a caree;
   storing the ECT public key and caree public key in the nonvolatile memory of a shared computing system for future use;
   transmitting the private key of the caree to the caree's endpoint communication device, storing it in nonvolatile memory of the caree's endpoint communications device for future use, and deleting the caree private key from working memory of the shared computing system;
   transmitting the private key of the ECT to each ECT member's endpoint communication device, storing it in nonvolatile memory of each ECT member's endpoint communication device for future use, and deleting the ECT private key from working memory of the shared computing system;
   receiving EHRs associated with the caree from at least one external service, encrypting the EHRs with the public key of the caree, and storing the encrypted EHRs in the nonvolatile memory of the shared computing system.

2. The method of claim 1 further comprising encrypting the private key of the caree using the public key of the ECT and storing the encrypted key in the nonvolatile memory of the shared computing system.

3. The method of claim 2 further comprising the shared computing system retrieving the encrypted private key of the caree from the nonvolatile memory of the shared computing system and transmitting it to each ECT member as they join the emergency call along with the caree's encrypted EHRs.

4. The method of claim 3 further comprising each ECT member's endpoint communication device decrypting the caree private key using the ECT private key.

5. The method of claim 4 further comprising each ECT member's endpoint communication device decrypting the caree EHRs using the caree private key for display to the ECT member.

6. A method for generating a new public key private key pair for a pre-established Emergency Care Team (ECT) associated with a caree, orchestrated by a backend system consisting of at least one instance of a computing element, working memory, and nonvolatile memory, when any change occurs to the ECT membership comprising:
   receiving notification by the backend system of a change in ECT membership or the loss of any ECT member's endpoint communications device;
   backend system generating a new public key private key for the ECT;
   backend system transmitting the new ECT private key to all ECT member endpoint communications device and deleting the ECT private key from working memory;
   storing the new ECT private key in each of the ECT member's endpoint communications device for future use;
   storing the new ECT public key in the nonvolatile memory of the backend system;
   backend system transmitting the new ECT public key to the caree's endpoint communication device over a broadband communications network;
   caree's endpoint communication device encrypting the caree's private key using the new ECT public key;
   caree's endpoint communication device transmitting the encrypted private key to the backend system;
   backend system storing the encrypted caree private key in nonvolatile memory for use in a future medical emergency.

7. A method of key recovery for a pre-established Emergency Care Team (ECT) associated with a caree, orchestrated by a backend system consisting of at least one instance of a computing element, working memory, and nonvolatile memory, an ECT consisting of individuals who have been invited to assist during an emergency event and who each possess an endpoint communication device such as but not limited to a mobile phone, a caree who possesses an endpoint communication device, each member of the ECT in possession of a private key common to the group, the backend system in possession of the public key for the ECT, and the backend system in possession of the caree private key encrypted using the ECT public key, to be used when a caree loses their private key comprising:

backend system receiving a message from the caree indicating the private key has been lost;

backend system broadcasting a message to all ECT members' endpoint communication device over the communications network requesting confirmation and assistance;

backend system receiving a reply from at least one ECT member endpoint communication device acknowledging ability to assist;

the ECT member communicating with caree through a different channel to confirm that it is indeed the request from the caree;

the ECT sending message to backend system to confirm that the request is truly from the caree;

backend system retrieving the stored caree encrypted private key from nonvolatile memory and transmitting the encrypted private key to the responding ECT member endpoint communication device;

the ECT member endpoint communication device decrypting the caree private key using their stored ECT private key;

the ECT member endpoint communication device encrypting the caree private key using their stored ECT private key and deleting the caree private from working memory;

the ECT member endpoint communication device transmitting this encrypted private key to the shared computing system in response to the request;

shared computing system transmitting the caree encrypted private key and the ECT public key to the caree endpoint communications device;

caree endpoint communication device decrypting the encrypted caree private key using the ECT public key;

caree endpoint communication device storing their private key for future use.

8. A method for creating, distributing, and persisting an immutable record of access during a medical emergency to the Electronic Health Records (EHRs) of a Person in Distress (PID) comprising:

creating a first block containing a unique identifier for the PID, date and time of the emergency event, and a copy of the EHRs as they existed at the time of the event encrypted with the private key of the PID;

creating at least one subsequent block containing the unique identifier for the person who accessed the EHRs, the human readable name of that person, the phone number of that person, and the date and time of access;

transforming the access record blocks into an immutable encrypted document;

sending a copy of this document to the endpoint devices of all members of the PID's Emergency Care Team (ECT) to be persisted in nonvolatile memory of the endpoint device for future use;

persisting a copy of this document in nonvolatile memory of the caree;

persisting a copy of this document in nonvolatile memory of the backend system.

9. The method of claim 8 comprising the use of blockchain technology to encode the access records.

10. A system comprising one or more processors and one or more memories;

The one or more processors configured to execute a program stored in the one or more memories to perform a method comprising:

generating a public key & private key associated with an Emergency Care Team (ECT);

generating a public key & private key associated a caree;

storing the ECT public key and caree public key in the nonvolatile memory of a shared computing system for future use;

transmitting the private key of the caree to the caree's endpoint communication device, storing it in nonvolatile memory of the caree's endpoint communications device for future use, and deleting the caree private key from working memory of the shared computing system;

transmitting the private key of the ECT to each ECT member's endpoint communication device, storing it in nonvolatile memory of each ECT member's endpoint communication device for future use, and deleting the ECT private key from working memory of the shared computing system;

receiving the Electronic Health Records (EHRs) associated with the caree from at least one external service, encrypting the EHRs with the public key of the caree, and storing the encrypted EHRs in the nonvolatile memory of the shared computing system.

* * * * *